United States Patent [19]

DeHoff

[11] Patent Number: 5,191,090
[45] Date of Patent: Mar. 2, 1993

[54] PREPARATION OF 2-(2'-THIENYL)ETHYLAMINE DERIVATIVES AND SYNTHESIS OF THIENO(3,2-C)PYRIDINE DERIVATIVES THEREFROM

[75] Inventor: Bradley S. DeHoff, Boulder, Colo.

[73] Assignee: Syntex (U.S.A.) Inc., Palo Alto, Calif.

[21] Appl. No.: 738,697

[22] Filed: Jul. 31, 1991

Related U.S. Application Data

[62] Division of Ser. No. 470,299, Jan. 25, 1990, Pat. No. 5,068,360.

[51] Int. Cl.$^5$ .................. C07D 333/26; C07D 495/01
[52] U.S. Cl. ........................................ 549/74; 546/114
[58] Field of Search ........................... 549/74; 546/114

[56] References Cited

U.S. PATENT DOCUMENTS

| | | | |
|---|---|---|---|
| 4,127,580 | 11/1978 | Braye | 546/114 |
| 4,128,561 | 5/1978 | Braye | 549/74 |
| 4,906,756 | 3/1990 | Lodewijk et al. | 546/111 |

FOREIGN PATENT DOCUMENTS

| | | |
|---|---|---|
| 873677 | 1/1978 | Belgium . |
| 0069002 | 9/1985 | European Pat. Off. . |
| 0274324 | 7/1988 | European Pat. Off. . |
| 61-221184 | 10/1986 | Japan . |
| 63-035546 | 2/1988 | Japan . |
| 63-104982 | 5/1988 | Japan . |

OTHER PUBLICATIONS

"α-Thienylaminoalkanes", Blicke et al., J. Amer. Chem. Soc., 64(3), 477-480 (1942).

"The Synthesis of Chemical Reactivity of Thieno[2,3-c]- and Thieno[3,2-c]pyridines", Dressler et al., J. Heterocyclic Chem., 7(6), 1257-1268 (1970).

"Nickel-Catalyzed Synthesis of Arylacetonitriles from Arylzinc Chlorides and Bromoacetonitrile", Frejd et al., Synthesis, 1, 40-42 (1987).

"Survey of Organic Synthesis", Buehler, C. A., Pearson, D. E., vol. 1, p. 448 (1970).

*Primary Examiner*—Richard L. Raymond
*Assistant Examiner*—Mark W. Russell
*Attorney, Agent, or Firm*—James J. Wong; David A. Lowin

[57] ABSTRACT

An improved process for the synthesis of 2-(2'-thienyl)ethylamine from suitably functionalized derivatives of 2-(2'-thienyl)ethanol employing ammonia gas in the presence of a metal salt or liquid ammonia and alkyl ketone as a solvent. The 2-(2'-thienyl)ethylamine produced by this process is advantageously converted to ticlopidine.

12 Claims, No Drawings

PREPARATION OF 2-(2'-THIENYL)ETHYLAMINE DERIVATIVES AND SYNTHESIS OF THIENO(3,2-C)PYRIDINE DERIVATIVES THEREFROM

CROSS-REFERENCE TO RELATED APPLICATION

This application is a division of allowed pending application Ser. No. 07/470,299, filed Jan. 25, 1990, now U.S. Pat. No. 5,068,360 incorporated herein by reference, which prior application is related to a co-pending application entitled "Carbamate Salts of 2-(2'-Thienyl)Alkylamines" which application is incorporated herein by reference and which application names as inventor Hiralal N. Khatri, a co-worker in the research organization as that of the present inventor. Said co-pending application is Ser. No. 470,018, filed contemporaneously herewith on Jan. 25, 1990, now U.S. Pat. No. 4,997,945.

BACKGROUND OF THE INVENTION

1. Field of the Invention

The present invention relates to processes for the synthesis of thieno[3,2-c]pyridine derivatives, particularly ticlopidine, and specifically to an improved process for conversion of suitably functionalized derivatives of 2-(2'-thienyl)ethanol to 2-(2'-thienyl)ethylamine.

2. Background Information

Ticlopidine is a compound with desirable blood platelet aggregation inhibition qualities. Previous technology for the preparation of ticlopidine has entailed a low yielding, labor intensive process, employing certain potentially hazardous and expensive materials. The cost of preparing ticlopidine has, therefore, been high. It has been desired to provide improved synthetic process technology that allows for a higher conversion, reduced labor usage, and the elimination of costly, potentially dangerous materials.

A variety of synthetic approaches to making ticlopidine have been described in the art, including improvements on the various steps of such synthetic processes, e.g., as described below.

Ticlopidine was first described by Castaigne in U.S. Pat. No. 4,051,141, where the synthesis thereof was accomplished by condensation of a thieno[3,2-c]pyridine with o-chlorobenzyl chloride.

One desirable method of preparing ticlopidine calls for 2-(2'-thienyl)ethylamine as a key intermediate. The method involved preparation of a 2-(2'-thienyl)ethanol, conversion to the corresponding sulfonate derivative and then to the amine, followed by cyclization and benzylation with o-chlorobenzyl-chloride to give ticlopidine free base, as described by Braye in U.S. Pat. No. 4,127,580.

Previous methods for the preparation of 2-(2'-thienyl)ethylamine have suffered from several disadvantages, including low yields (e.g., where the reactions resulted in mixtures of undesirable side products) and high cost.

For example, Braye, U.S. Pat. No. 4,128,561 describes a two-step process of making 2-(2'-thienyl)ethylamine by converting 2-(2'-thienyl)ethanol to N-2-(2'-thienyl)ethyl phthalimide, and then treating the phthalimide with diethylenetriamine to form the amine. Braye also describes the amination of 2-(2'-thienyl)alkyl sulfonates with ammonia at elevated temperature and pressure. Braye discloses problems encountered in the preparation of primary amines with ammonia, i.e., the tendency for the process to form secondary and tertiary amines as side products.

A process where 2-(2'-thienyl)ethylbromide is treated with alcoholic ammonia at ordinary temperature for 8 days to produce 2-(2'-thienyl)ethylamine is described by Blicke, et al., J. Am. Chem. Soc., 64, 3, 477–480 (1942).

Generally, the synthesis of primary amines with ammonia has been found to be disadvantageous because primary amines are more basic than ammonia; this will cause the primary amine to preferentially attack the reaction substrate over the ammonia, resulting in the formation of secondary and tertiary amines. Advanced Organic Chemistry, March, J., 2nd Ed., 376, (1977). Such formation of undesired secondary and tertiary amines, of course, reduces the yield of the desired primary amine and creates the need for additional purification and isolation steps, which further decrease the yield and increase the cost of the desired primary amine. The formation of undesired secondary and tertiary amines has remained a problem until the present invention.

Other synthetic approaches to making 2-(2'-thienyl)ethylamine have been disclosed in the art, for example, as described below.

The reduction of 2-(2'-thienyl)acetamide with a hydride, e.g., lithium aluminum hydride to form 2-(2'-thienyl)ethylamine is described in Japanese Kokai J6 1221-184-A.

The electrochemical reduction of 2-nitro-2-vinyl thiophene to 2-amino-2-ethyl-thiophene is described in UK Patent Application GB 2,013,196A.

The catalytic hydrogenation of thienyl acetonitrile to form thienyl ethylamines is described in European Patent No. 274,324.

The reduction of nitrovinyl thiophenes with a hydride, e.g., lithium aluminum hydride to form thiophene ethylamines is described in J. Heterocyclic Chem., 7, 1257–1268 (1970).

The reduction of arylacetonitriles with lithium aluminum hydride/aluminum chloride to form the corresponding 2-aryl-1-aminoethanes is described in Synthesis, 1, 40–42, (1987).

SUMMARY OF THE INVENTION

One aspect of the present invention relates to a process in which ammonia gas is contacted with a suitably functionalized derivative of 2-(2'-thienyl)ethanol, preferably a halide, alkyl or arylsulfonate in the presence of a metal salt, to form 2-(2'-thienyl)ethylamine, the compound of Formula I.

In another aspect, the invention relates to a process in which liquid ammonia is contacted with a suitably functionalized derivative of 2-(2'-thienyl)ethanol, preferably a halide, aklyl or arylsulfonate in a ketonic solvent, preferably an alkyl ketone or aryl ketone, to form 2-(2'-thienyl)ethylamine, the compound of Formula I.

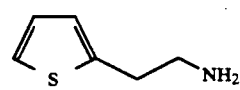

Formula I

In another aspect, the invention relates to a process for synthesis of thieno[3,2-c]pyridine derivatives of Formula II (where n is 1 or 2, and R is a phenyl or benzoyl radical optionally substituted with 1-3 halogen atoms, alkyl having 1-6 carbon atoms, alkoxy having 1-6 carbon atoms, hydroxy or with nitro) and the pharmaceutically acceptable salts thereof, from the 2-(2'-thienyl)ethylamine so-prepared.

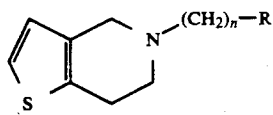

Formula II

In still another aspect, the invention relates to a process for the synthesis of ticlopidine hydrochloride (shown as Formula III, a salt within the scope of Formula II) from the 2-(2'-thienyl)ethylamine so-prepared.

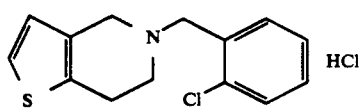

Formula III

In other aspects, the invention relates to thieno[3,2-c]pyridine derivatives made by the process of the invention, particularly ticlopidine.

DETAILED DESCRIPTION OF THE INVENTION

Definitions and General Parameters

The following definitions are set forth to illustrate and define the meaning and scope of the various terms used to describe the invention herein.

A "pharmaceutically acceptable acid addition salt" of the thieno[3,2-c]pyridine derivatives may be any salt derived from an inorganic or organic acid, e.g., ticlopidine hydrochloride. The term "pharmaceutically acceptable anion" refers to the anion of such acid addition salts. The salt and/or the anion are chosen not to be biologically or otherwise undesirable. The anions are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, salicylic acid, methanesulfonic acid, ethanesulfonic acid, p-toluensulfonic acid and the like.

As used herein, the term "halo" refers to fluoro, bromo, chloro and iodo.

As used herein, the term "alkyl ketone" refers to a ketonic solvent where the carbonyl group is connected to alkyl radicals, i.e., a fully saturated monovalent radical containing only carbon and hydrogen, e.g., methyl, ethyl, propyl, butyl, pentyl, hexyl, and heptyl; and which may be cyclic, branched or straight chain. This term is further exemplified by acetone, methylethyl ketone, diethyl ketone and cyclohexanone.

As used herein, the term "aryl ketone" refers to a ketonic solvent where the carbonyl group is connected to at least one aryl radical, i.e., a monovalent unsaturated aromatic carbocyclic radical having a single ring, e.g., phenyl; or two rings, e.g., naphthyl This term is further exemplified by diphenyl ketone and methylphenyl ketone.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), choroform, methylene chloride (or dichloromethane), diethyl ether, methanol, ethanol, water, pyridine and the like]. Unless specified to the contrary, the solvents used in the reactions of the present invention are inert organic solvents.

As used herein, "leaving group" means an atom or a group, charged or uncharged, that is detachable from an atom in what is considered to be the residual or main part of a molecule, including such leaving groups as, halo, alkyl sulfonates, aryl sulfonates, phosphates, sulfonic acid and sulfonic acid salts.

Unless specified to the contrary, the reactions described herein take place at atmospheric pressure over a temperature range from about 10° C. to about 100° C., more preferably from about 10° C. to about 50° C., and most preferably at about room (or "ambient") temperature, e.g., about 20° C.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "effective amount" means a dosage sufficient to provide treatment for the disease state being treated. This will vary depending on the patient, the disease and the treatment being effected See, for example, Castaigne U.S. Pat. 4,051,141 (the pertinent portions of which are incorporated herein by reference), for a detailed description of the anti-inflammatory activity, vaso-dilator activity, and inhibitory activity on blood plate aggregation of the thieno[3,2-c]pyridine derivatives made according to the present invention, as well as the description of toxicological and pharmacological investigations therefor.

Synthesis of the Compounds of Formulae I, II and III

The compounds of Formulae I, II and III are synthesized as described with reference to Reaction Schemes 1 to 5.

Reaction Scheme 1 illustrates the conversion of suitable derivatives of 2-(2-thienyl)ethanol to form 2-(2'-thienyl)ethylamine.

Reaction Scheme 2 illustrates an alternative synthetic route for the conversion of suitable derivatives of 2-(2'-thienyl)ethanol to form 2-(2'-thienyl)ethylamine.

Reaction Scheme 3 illustrates the conversion of 2-(2'-thienyl)ethylamine to and from its carbamic acid salt.

Reaction Scheme 4 illustrates the conversion of 2-(2'-thienyl)ethylamine to thieno[3,2-c]pyridine derivatives by benzylation of 4,5,6,7-tetrahydrothieno[3,2-c]pyridine.

Reaction Scheme 5 illustrates an alternate synthetic route for the conversion of 2-(2'-thienyl)ethylamine to thieno[3,2-c]pyridine derivatives by benzylation of 2-(2'-thienyl)ethylamine followed by cyclization.

Preparation of 2-(2'-thienyl)ethylamine (I)

2-(2-Thienyl)ethanol and its suitable derivatives, e.g., benzenesulfonate and methanesulfonate are prepared according to the procedure of Braye U.S. Pat. No. 4,127,580. In addition, 2-(2-thienyl)ethanol is commercially available from Henley Chemicals, 50 Chestnut Ridge Road, Montvale, N.J., 07645.

Ammonia gas of sufficient purity, Anhydrous Grade, is commerically available from Matheson Gas Products, P.O. Box 85, East Rutherford, N.J., 07073.

Metal salts useful in the process of the present invention are represented by the formula M-Y, where M is selected from Na, Li, K, Mg, and Zn, and Y is halo or a carbonate ($CO_3^{-2}$) anion. These salts are commercially available, e.g., from Aldrich Chemicals, 940 West Saint Paul Avenue, Milwaukee, Wis. 53233. MgI is commercially available from Hudson Laboratories, 13923 Old Dixie Highway, Hudson, Fla. 33567.

Reaction Scheme 1

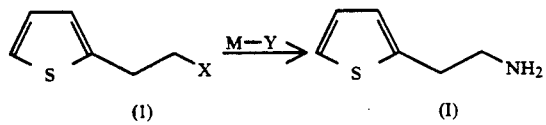

As illustrated in Reaction Scheme 1, a suitably functionalized derivative of 2-(2'-thienyl)ethanol, i.e., a compound of Formula 1 where X is alkyl sulfonate, aryl sulfonate or halogen, preferably 2-(2'-thienyl)ethyl benzenesulfonate or 2-(2'-thienyl)ethyl methanesulfonate, and about 1 molar equivalent of a metal salt of formula M-Y is dissolved in a solvent (e.g., a polar solvent such as tetrahydrofuran, toluene, water, methanol or ethanol, preferably methanol) is placed in a pressurizable reactor. The pressure reactor is rapidly pressurized to about 25-150 psi, preferably about 80 psi with ammonia gas while keeping the internal temperature at about 45°-60° C., preferably 50°-55° C., and the solution is stirred for 2-20 hours, preferably 12-16 hours, under ammonia gas.

Alternatively, the functionalized derivative of 2-(2'-thienyl)ethanol, i.e., a compound of Formula 1 where X is alkyl sulfonate, aryl sulfonate or halogen, preferably 2-(2'-thienyl)ethyl benzenesulfonate or 2-(2'-thienyl)ethyl methanesulfonate, can be added into the pressurized reactor using a positive displacement pump. This is preferable at larger scales.

The contents are made acidic, preferably to about pH 2, and extracted, preferably twice with a nonpolar solvent, preferably $CH_2Cl_2$. The aqueous layer is collected and made basic, preferably to about pH 10-11, and extracted, preferably three times, with a nonpolar solvent, preferably $CH_2Cl_2$. The organic layers containing the amine are combined and dried over a dessicant agent, preferably sodium sulfate, and concentrated to give the desired 2-(2'-thienyl)ethylamine as an oil.

Alternatively, water is added to the reaction mixture and the mixture is extracted three times with a nonpolar solvent (e.g., $CH_2Cl_2$) and dried over $Na_2SO_4$. The solvent is removed and the oil is purified by distillation (boiling point 90°-95° C. at 4.5mm/Hg) or by precipitation as its carbamic acid salt as described below.

Reaction Scheme 2

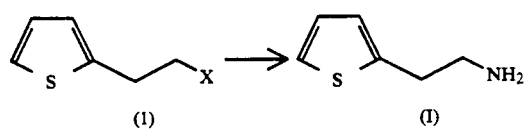

Alternate Preparation of Formula I

An alternative preparation of the compounds of Formula I is illustrated above in Reaction Scheme 2, where a pressure reactor is charged with a suitably functionalized derivative of 2-(2'-thienyl)ethanol, i.e., a compound of Formula 1 where X is alkyl sulfonate, aryl sulfonate or halogen, preferably 2-(2'-thienyl)ethyl methanesulfonate; and a ketonic solvent, such as, an alkyl ketone, acetone, methylethyl ketone, diethylketone, cyclohexanone, or aryl ketone, such as, diphenyl ketone, methylphenyl ketone, most preferably, acetone, at a molar excess, preferably, at a two to one ratio (molar equivalents) to starting material. Liquid ammonia is added to the pressure reactor, at a molar excess, preferably, at a twenty to one ratio (molar equivalents) to the methanesulfonate. The pressure reactor is sealed and allowed to heat up to about 15° C. to 35° C., preferably, 25° C., without external heating. The mixture is stirred for about 12 hours. The ammonia is released as a gas. The acetone is removed by distillation, and the contents are refluxed for about 1 hour.

The contents are made basic to about pH 10 by the addition of solid NaOH. The mixture is extracted three times with a non-polar solvent (e.g., hexane). The organic layer is dried over a dessicating agent, preferably, sodium sulfate The solvent is removed.

Alternatively, the tertiary amine by-product, can be removed by first making the contents acidic, e.g., upon the addition of HCl, tertiary amine precipitates out as a HCL salt and is removed by filtration. The contents are then made basic to about pH 10, e.g., by the addition of solid NaOH, followed by the extraction procedure disclosed above.

Preparation of 2-(2'-thienyl)ethylamine carbamic acid salt

In a presently preferred process, the 2-(2'-thienyl)ethylamine prepared as described above is converted to the carbamic acid salt, to facilitate storage and handling. This process is the subject of separate copending application, Serial No. 470,018 now U.S. Pat. No. 4,997,945, filed contemporaneously herewith by a coworker in the same research organization as that of the present inventor, incorporated herein by reference.

Reaction Scheme 3

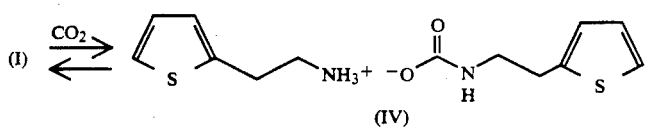

In order to prepare the carbamic acid salt, as illustrated in Reaction Scheme 3, 2-(2'-thienyl)ethylamine oil (I) is dissolved in a solvent, preferably a combination of hexanes with toluene (ratio of about 5 to 1, or 4 to 1) and cooled, preferably to about 0° C. $CO_2$, as a gas or a solid, contacted with the solution for about one half to 3 hours, preferably 1–2 hours, the carbamic acid salt of the amine is collected as a precipitate.

2-(2'-Thienyl)ethylamine is readily converted from its solid carbamic acid salt and is suitable, without further purification, for use in the synthesis of the thieno[3,2-c]pyridine derivatives, particularly ticlopidine, for example as described below.

The carbamic acid salt is converted to the free amine by dissolving the acid salt in water and warming it to about 65° C. The carbamic acid salt begins losing $CO_2$ at 60° C. When conversion is complete (the loss of $CO_2$ ceases) the solution is allowed to cool to room temperature.

Reaction Scheme 4

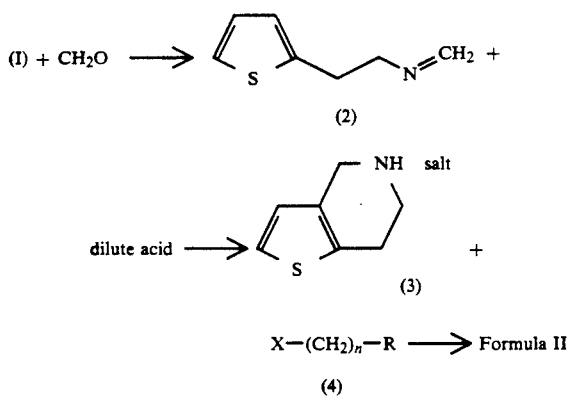

Preparation of 4,5,6,7-Tetrahydrothieno[3,2-c]pyridine (3)

4,5,6,7-Tetrahydrothieno[3,2-c]pyridine can be prepared according to the procedure of Gronowitz et al. [*Arkiv Kemi*, 13(19), 217–227 (1970)] incorporated herein by reference.

As illustrated in Reaction Scheme 4, a slight molar excess of formaldehyde (e.g., a 37% aqueous solution) is added dropwise with stirring to 2-(2'-thienyl)ethylamine (I). The reaction mixture is stirred for about 1 to 5 hours, preferably about 3 hours, at the reflux temperature of the solvent used. After cooling to room temperature, the product is extracted, e.g., into toluene (or another solvent such as dichloromethane, chloroform, or ethyl acetate), washed and concentrated in vacuo to give the formimine of 2-(2'-thienyl)ethylamine (a 90–95% yield of the compound of Formula 2).

The formimine (2) is shaken with a dilute solution of an aqueous acid (such as hydrochloric acid or sulfuric acid) or a solution of formamine (2) dissolved in an organic solvent such as THF or toluene, preferably THF, is shaken with an organic acid (such as formic acid, oxalic acid, paratoluene sulfonic acid or methane sulfonic acid; preferably methane sulfonic acid) for 3 to 10 hours, preferably about 6 hours. The mixture is then basified (e.g., with NaOH) and extracted, e.g., with methylene chloride (or another solvent). The extracts are washed and concentrated in vacuo to give 4,5,6,7-tetrahydrothieno[3,2-c]pyridine (a 80–90% yield of the compound of Formula 3).

Preparation of Formula II

Still referring to Reaction Scheme 4, a solution of 4,5,6,7-tetrahydrothieno[3,2-c]pyridine in a solvent (e.g., a polar solvent, such as THF, dichloromethane or acetonitrile; preferably THF) is added to a molar excess of a suspension of a base (e.g., a metal hydride, such as lithium hydride, 50% sodium hydride, or potassium hydride; preferably, 50% sodium hydride) in the same or a similar solvent. The mixture is stirred at a temperature of about 15° to 30° C., preferably about room temperature for about 10 minutes to about 2 hours, preferably about 30 minutes and a slight molar excess (e.g., a ratio of about 1.1 to 0.7) of an optionally substituted phenalkyl or phenacyl halide of Formula 4 [where X is halo, n is 1 or 2, and R is a phenyl or benzoyl radical optionally substituted with 1–3 halogen atoms or alkyl having 1–6 carbon atoms, alkoxy having 1–6 hydroxy or carbon atoms, or nitro, (for example the halides of Formula III in U.S. Pat. No. 4,051,141, such as 4-methoxybenzyl chloride, phenacyl bromide, or preferably o-chlorobenzyl chloride)] is added.

After stirring at about room temperature, for about 1 to 2 hours, preferably about 90 minutes, the mixture is heated, preferably to the reflux temperature of the solvent used. Another solvent (e.g., toluene, xylene, or ether; preferably toluene) is added and the mixture is further refluxed for about 2 to 48 hours, preferably for about 10 to 30 hours, most preferably about 20 hours. The mixture is then cooled to about room temperature and acidified (e.g, with dilute hydrochloric acid or acetic acid; preferably hydrochloric acid).

The organic layer separated, the aqueous layer is extracted (e.g., with toluene, dichloromethane, ethyl acetate, or i-propyl acetate; preferably toluene) and the combined aqueous layers are basified (e.g., with aqueous NaOH or solid NaOH) to a pH of about 13–14. The product is extracted, e.g., into methylene chloride (or another solvent). The extracts are washed (e.g., with water optionally including a salt solution), dried and then concentrated in vacuo to give a compound of Formula II.

When the compound of Formula 4 is o-chlorobenzyl chloride, ticlopidine free base (Formula III) is formed (about 80% yield) as a light yellow oil.

Phase Transfer Alkylation

Alternatively, the alkylation can be performed under phase transfer conditions, e.g., as described in GB 2,166,730, the pertinent parts of which are incorporated herein by reference. The 4,5,6,7-tetrahydrothieno[3,2- c]pyridine (3) and compound of Formula 4 (preferably o-chlorobenzyl chloride) are dissolved in a solvent system (preferably an aqueous:organic two-phase solvent system, the organic phase of which is immiscible with water, e.g., hydrocarbons such as benzene, toluene and xylene; and ethers such as isopropyl ether and diethyl ether; preferably toluene) combined with a phase transfer catalyst [e.g., a quaternary ammonium salt, such as trimethylbenzyl ammonium hydroxide, hydrogen sulfate tetra-n-butyl ammonium, trioctylmethyl ammonium chloride, triethylbenzyl ammonium chloride or tert-butyl ammonium iodide ("TBAI"), or a phosphonium salt, such as tetrabutyl phosphonium chloride, or a crown ether, such as 18-crown-6 or dibenzo 18-crown-6; preferably TBAI] in the presence of a base [e.g., sodium hydroxide, potassium hydroxide, lithium hydroxide, potassium carbonate, sodium carbonate, or sodium hydride; preferably sodium hydroxide] and stirred for about 24 to 72 hours, preferably about 40 hours, at room temperature The product (75% of theoretical yield) is separated, concentrated, and purified by the usual means.

Preferred Alkylation

In a preferred alkylation procedure, 4,5,6,7-tetrahydrothieno[3,2-c]pyridine in a solvent (e.g., a polar solvent, such as THF, dichloromethane or acetonitrile; preferably 5-15% wet THF) and a compound of Formula 4 (preferably o-chlorobenzyl chloride) are added to a molar excess of a base (e.g., potassium carbonate, sodium carbonate, or lithium carbonate; preferably potassium carbonate) that has been wetted with water (about 5 to 15%, preferably about 10% of the volume charge) and the reaction mixture is refluxed until disappearance of the starting materials is confirmed by tlc (about 8 to 42 hours, preferably about 18-24 hours). The solvent is removed (by vacuum or by displacement with another solvent such as toluene), and the product is washed with water and then concentrated in vacuo. Using the preferred compound of Formula 4, ticlopidine free base (Formula III) is formed (about 90-95% yield) as a light yellow oil.

Reaction Scheme 5

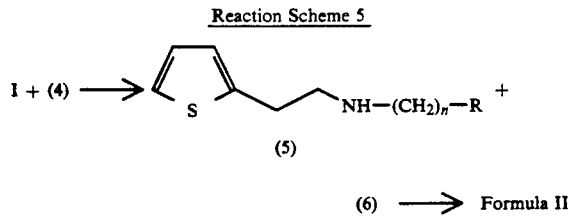

Alternate Preparation of Formula II

Alkylation of 2-(2'-thienyl)ethylamine, Followed by Cyclization

Another alternative preparation of the compounds of Formula II is illustrated above in Reaction Scheme 5, where the compound of Formula I, prepared as described above with reference to Reaction Scheme 1, is contacted with a compound of Formula 4 under the conditions described above to give the secondary amine of Formula 5, which is in turn cyclized by contacting it with a compound identified in Reaction Scheme 5 as Formula 6 (i.e., formaldehyde, paraformaldehyde, trioxane or a compound of Formula III of U.S. Pat. No 4,174,448, such as dimethoxymethane) under the conditions described in U.S. Pat. No. 4,174,448, the pertinent portions of which are incorporated herein by reference.

Preparation of the Salts of Formula II

Some of the compounds of Formula II may be converted to corresponding acid addition salts. The conversion is accomplished by treatment with a stoichiometric amount of an appropriate acid, such as hydrochloric acid, sulfuric acid, methanesulfonic acid, HBr, or the like (for tyclopidine the preferred acid is hydrochloric). Typically, the free base is dissolved in a polar organic solvent such as ethanol or methanol, and the acid is added in water, ethanol or methanol. The temperature is maintained at 0°-50° C. The resulting salt precipitates spontaneously or may be brought out of solution with a less polar solvent (such as toluene, ether, or ethyl acetate; preferably toluene).

Preferably, for making ticlopidine hydrochloride, about 1.3 equivalents of gaseous hydrogen chloride is bubbled into isopropanol, which is then added slowly with stirring to ticlopidine free base in toluene, maintaining the temperature below about 40° C. during the addition. The stirring is continued for about 30 to 90 minutes, preferably about 1 hour at about 45°-50° C., followed by cooling to about 5°-10° C. for about 30 to 90 minutes, preferably about 1 hour, and the ticlopidine hydrochloride precipitates. It is isolated (e.g., by centrifugation), digested (e.g., with toluene and isopropanol, or preferably with acetone), dried (e.g., at about 65 to 70° C. under vacuum), and recrystallized from a lower alkanol (e.g., methanol, ethanol or isopropanol).

The acid addition salts of the compounds of Formula II may be converted to the corresponding free bases by treating with an excess of a suitable base, such as ammonia or sodium bicarbonate, typically in the presence of aqueous solvent and at a temperature of between 0° and 50° C. The free base form is isolated by conventional means, such as extraction with an organic solvent.

Preferred Processes and Last Steps

A preferred process for making 2-(2'-thienyl)ethylamine, comprises reacting a suitably functionalized derivative of 2-(2'-thienyl)ethanol, more preferably the benzenesulfonate or methanesulfonate, with ammonia gas in the presence of a metal salt, preferably NaBr.

Another preferred process for making 2-(2'-thienyl)ethylamine, comprises reacting a suitably functionalized derivative of 2-(2'-thienyl)ethylethanol, more preferably the benzenesulfonate or methanesulfonate, with liquid ammonia in an alkyl ketone, preferably, acetone.

A preferred process for making ticlopidine comprises the steps of:
  a. reacting a suitably functionalized derivative of 2-(2'-thienyl)ethanol with ammonia gas in the presence of a metal salt to give 2-(2'-thienyl)ethylamine, and
  b. converting the 2-(2'-thienyl)ethylamine to ticlopidine.

In the above-described preferred process for making ticlopidine, further preferred is the process wherein the step of converting the 2-(2'-thienyl)ethylamine to ticlopidine comprises the steps of:
  c. contacting said 2-(2'-thienyl)ethylamine with formaldehyde to give the formimine;
  d. cyclizing said formimine by contacting it with an aqueous mineral acid to form 4,5,6,7-tetrahydrothieno[3,2-c]pyridine; and e. alkylating said 4,5,6,7-tetrahydrothieno[3,2-c]pyridine to give ticlopidine, by contacting it with o-chlorobenzyl chloride under either:
   (i) phase transfer conditions, or
   (ii) preferably, by reflux with a base, most preferably potassium carbonate, using conventional alkylation conditions.

Further preferred is the above process wherein the 2-(2'-thienyl)ethylamine so-prepared is converted to its carbamic acid salt for storage, transportation, handling and/or further purification, and converted back to 2-(2'-thienyl)ethylamine for subsequent use in step c as described above.

Most preferred is the above processes comprising the additional step of converting the ticlopidine so-made to the hydrochloride salt.

Preferred Compounds

The preferred compounds made by the process of the invention are 2-(2'-thienyl)ethylene and 5-(2-chlorobenzyl)-4,5,6,7-tetrahydrothieno-[3,2-c]pyridine, which is also known as ticlopidine. Particularly preferred is ticlopidine hydrochloride.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

Preparation of 2-(2'-thienyl)ethylamine (TEA)

1A. Preparation from 2-(2'-thienyl)ethylbenzenesulfonate

A 1 liter Parr pressure reactor is charged with 70 g of 2-(2'-thienyl)ethyl benzenesulfonate, 250 ml of methanol, 50 ml of concentrated aqueous ammonium hydroxide and 26.4g of sodium bromide (sodium bromide is about 90% soluble after a few minutes of stirring). The reactor was pressurized to 80 psi with ammonia gas while maintaining the internal temperature at 50° C. and is stirred overnight at the same conditions. The contents are acidified to about pH 2 and extracted twice with methylene chloride. The aqueous layer is made basic to about pH 10-11 with sodium hydroxide pellets and extracted three times with methylene chloride. The combined organic layers, containing the TEA, are dried over sodium sulfate and concentrated to an oil. The TEA oil is about 55-60% pure by gas chromatography.

1B. Preparation of the carbamic acid salt

The oil is dissolved in hexane/toluene (4:1) and cooled to 0° C. Carbon dioxide gas is bubbled through the solution for 2 hours. The precipitated solids are collected and analysed by gas chromatography.

Following the above procedure, there was obtained 25.7 g (about 67% yield) of the carbamate salt, at an internal standard of purity of 100%.

EXAMPLE 2

Preparation of 2-(2-thienyl)ethylamine (TEA)

2A. Alternative preparation from 2-(2'-thienyl)ethylmethanesulfonate

A 1 liter Parr pressure reactor is charged with 51.7 g of 2-(2'-thienyl)ethyl methanesulfonate, 25.9 g of NaBr, 200 ml of methanol, 100 ml of concentrated aqueous ammonium hydroxide and 25.9 g of sodium bromide. The contents are cooled to about 10° C. and the reactor is pressurized to 80 psi with ammonia gas The reactor temperature is brought up to 50° C. while maintaining 80 psi of ammonia and stirred for 16 hours. The ammonia gas is released. The contents are acidified to about pH 2 and extracted twice with methylene chloride. The aqueous layer is made basic to about pH 10-11 with sodium hydroxide pellets and extracted three times with methylene chloride. The combined organic layers, containing the TEA, are dried over sodium sulfate and concentrated to an oil. The TEA oil is 70% pure by gas chromatography.

2B. Preparation of the Carbamic Acid Salt

The oil is dissolved in hexane/toluene (5:1) and cooled to about 5° C. Carbon dioxide gas is bubbled through the solution for 1 hour. The precipitated solids are collected.

Following the above procedure, there is obtained 37.6 g (about 80% yield) of the carbamic salt, at an internal standard of purity of 99.7%.

EXAMPLE 3

3A. Alternative preparation of 2-(2-thienyl)ethylamine (TEA) using liquid ammonia A pressure reactor is charged with 189 mmoles of 2-(2'-thienyl)ethyl methanesulfonate and 378 mmoles of acetone. The contents are cooled below $-33°$ C. and 150 mL of liquid ammonia is added The reactor is sealed and the contents are allowed to warm to 25° C. without external heating. The mixture is stirred overnight. The ammonia is released and the contents are transferred to a flask. The acetone is removed by distillation up to 85° C. The contents are refluxed for 1 hour. The contents are made basic to pH 10 by adding solid NaOH. The organic layer is dried over $Na_2SO_4$ and the hexanes are stripped off. Kugelrohr distillation gave a 78% yield of 90.2% purity TEA.

3B. Alternative preparation of 2-(2'-thienyl)ethylamine (TEA) using liquid ammonia By following the procedure of Example 3A and substituting diphenyl ketone for acetone TEA is obtained in similar yield and purity.

3C. Preparation of the Carbamic Acid Salt

The resulting oil can be collected in solid form by following the methods and procedures discussed in Examples 1 and 2.

EXAMPLE 4

Preparation of Ticlopidine

4A. Formimine of 2-(2'-Thienyl)ethylamine

A 37% aqueous formaldehyde solution (2.7 g, 0.033 mole) is added dropwise with stirring to 3.4 g (0.027 mole) of 2-(2'-thienyl)ethylamine obtained, e.g., by warming 4 g (0.0135 mole) of carbamic acid salt (2 mole of amine/mole of salt) in 8 ml of $H_2O$ at 45° C. The reaction mixture is stirred for three hours at reflux. After cooling to room temperature, the product is extracted into toluene (2×50 ml); the toluene extracts are washed with water (50 ml) and concentrated to give the desired product.

Following the above procedure, there is obtained 3.4 g (91%) of the formimine of 2-(2'-thienyl)ethylamine. Reported NMR (CDCl₃) w: 7.2-6.8 (m,3H), 3.46 (s,2H), 3.0-2.7 (m,4H).

4B. 4,5,6,7-tetrahydrothieno[3,2-c]pyridine

The formimine of 2-(2'-thienyl)ethylamine, prepared, for example, as described in Example 4A is shaken with 7 ml of 6N hydrochloric acid for six hours. The mixture is basified with 60 ml sodium hydroxide and extracted with 3×70 ml methylene chloride. The methylene chloride extracts are washed with water (1×50 ml) and concentrated to give the desired product.

Following the above procedure, there is obtained 3.4 g (about 100%) of crude 4,5,6,7-tetrahydrothieno[3,2-c]pyridine.

Reported NMR (CDC₁₃) w: 7.06 (d,1H), 6.72 (d,1H), 3.9 (br.s,2H), 3.2-2.7 (m,4H), 2.10 (br.s,-NH).

4C. Ticlopidine Free Base

To a suspension of sodium hydride (0.42 g, 8.6 mmole) in THF (5.0 ml) is added a solution of 4,5,6,7-tetrahydrothieno[3,2-c]pyridine (1.0 g, 7.2 mmole), prepared, for example, as described in Example 4B, in THF (10 ml). The mixture is stirred under a nitrogen atmosphere at room temperature for 30 minutes and o-chlorobenzyl chloride (1.74 g, 10.8 mmole) is added. After stirring at room temperature for 90 minutes, toluene (15 ml) is added and the mixture is heated to reflux for 15 to 20 hours. Disappearance of starting material is confirmed by TLC. The mixture is then cooled to room temperature and acidified with 40 ml 1N hydrochloric acid. The organic layer is separated. The aqueous layer is extracted with 50 ml of toluene. The aqueous layer is then separated and basified with dilute aqueous sodium hydroxide to pH 13-14. The product is extracted into methylene chloride (3×40 ml). The methylene chloride extracts are washed (1×50 ml water) and (1×50 ml salt solution) then dried over anhydrous magnesium sulfate and concentrated to give the desired product.

Following the above procedure, there is obtained 1.5 g (80%) of 5-(2-chlorobenzyl)-4,5,6,7-tetrahydrothieno[3,2-c]pyridine (ticlopidine free base) as a light yellow oil.

Reported NMR (CDCl₃) w: 7.7-7.15 (m,4H), 7.05 (d,1H), 6.65 (d,1H), 3.8 (s,2H), 3.6 (s,2H), 2.85 (br.s,4H).

4D. Ticlopidine Hydrochloride

Gaseous HCl (0.22 g, 0.006 mole) is bubbled into 50 ml isopropanol. The resulting solution is added dropwise to ticlopidine free base (1.5 g, 0.005 mole) in 50 ml toluene, prepared, for example as described in Example 4C, maintaining the temperature below 40° C. during the addition. The reaction mixture is stirred for 1 hour, cooled to about 5°-10° C. for 1 hour, and the precipitate separated by centrifugation. An acetone slurry is made of the precipitate, brought to reflux for 1 hour, and cooled to about 5°-10° C. for 1 hour. The precipitate, ticlopidine hydrochloride (Formula III), is separated by centrifugation, dried at 65°-70° C. under vacuum, and recrystallized from methanol (m p 206.5°-207.5° C.)

4E. Other Compounds of Formula II

By following the procedure of Example 4C and substituting for o-chlorobenzyl chloride the following:
m-chlorobenzyl chloride,
o-bromobenzyl bromide,
3,4,5-trimethoxybenzyl chloride, phenacyl bromide, and
o-methoxyphenacyl bromide;
there are obtained the following respective compounds:
5-(3-chlorobenzyl)-4,5,6,7-tetrahydrothieno[3,2-c]pyridine,
5-(2-bromobenzyl)-4,5,6,7-tetrahydrothieno[3,2-c]pyridine,
5-(3,4,5-trimethoxybenzyl)-4,5,6,7-tetrahydrothieno[3,2-c]pyridine,
5-phenacyl-4,5,6,7-tetrahydrothieno[3,2-c]pyridine, and
5-(o-methoxyphenacyl)-4,5,6,7-tetrahydrothieno[3,2-c] pyridine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for making 2-(2'-thienyl)ethylamine comprising contacting a compound of the formula

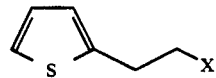

where
X is a leaving group;
with liquid ammonia; and
an alkyl ketone or aryl ketone.

2. The process of claim 1 wherein the ketone is selected from a group consisting of acetone, diethyl ketone, methylethyl ketone, methylphenyl ketone, diphenyl ketone and cyclohexanone.

3. The process of claim 1 wherein X is selected from the group consisting of halo, alkylsulfonate and arylsulfonate.

4. The process of claim 1 carried out at elevated pressure and temperature.

5. The process of claim 1 wherein X is methanesulfonate.

6. The process of claim 1 wherein the alkyl ketone is acetone.

7. A process for making ticlopidine, said process comprising the steps of:
a. reacting a compound of the formula

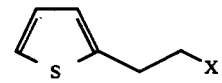

where
X is a suitable leaving group;
with liquid ammonia;
an alkyl ketone or aryl ketone; and
b. converting said 2-(2'-thienyl)ethylamine to ticlopidine.

8. The process of claim 7 comprising the additional step of converting said ticlopidine to the hydrochloride salt.

9. The process for making ticlopidine of claim 7 wherein said step of converting said 2-(2'-thienyl)ethylamine to ticlopidine comprises the steps of:
   a. contacting said 2-(2'-thienyl)ethylamine with formaldehyde to give the formimine;
   b. cyclizing said formimine by contacting it with aqueous hydrochloric acid to form 4,5,6,7-tetrahydrothieno[3,2-c]pyridine; and
   c. alkylating said 4,5,6,7-tetrahydrothieno[3,2-c]pyridine to give ticlopidine, by contacting it with o-chlorogenzyl chloride under either:
      (i) phase transfer conditions, or
      (ii) by reflux with a base.

10. The process for making ticlopidine of claim 9 wherein said alkylation (step e.) comprises contacting said 4,5,6,7-tetrahydrothieno[3,2-c]pyridine with a base selected from the group including potassium carbonate, sodium carbonate and lithium carbonate, using conventional alkylation conditions.

11. The process of claim 9 comprising the additional step of converting said ticlopidine to the hydrochloride salt.

12. The process of claim 10 comprising the additional step of converting said ticlopidine to the hydrochloride salt.

* * * * *